(12) United States Patent
Bott et al.

(10) Patent No.: US 8,338,596 B2
(45) Date of Patent: Dec. 25, 2012

(54) PROCESS FOR THE PREPARATION OF 5-SUBSTITUTED-8-ALKOXY[1,2,4]TRIAZOLO[1,5-C]PYRIMIDIN-2-AMINES

(75) Inventors: Craig Bott, Clare, MI (US); Christopher T. Hamilton, Midland, MI (US); Gary Alan Roth, Midland, MI (US)

(73) Assignee: Dow Agrosciences LLC, Indianapolis, IN (US)

( * ) Notice: Subject to any disclaimer, the term of this patent is extended or adjusted under 35 U.S.C. 154(b) by 0 days.

(21) Appl. No.: 13/325,809

(22) Filed: Dec. 14, 2011

(65) Prior Publication Data
US 2012/0088913 A1    Apr. 12, 2012

Related U.S. Application Data

(62) Division of application No. 13/114,087, filed on May 24, 2011.

(60) Provisional application No. 61/347,968, filed on May 25, 2010.

(51) Int. Cl.
*C07D 487/04* (2006.01)
(52) U.S. Cl. .................................................... 544/263
(58) Field of Classification Search .................. 544/263
See application file for complete search history.

(56) References Cited

U.S. PATENT DOCUMENTS

| 5,858,924 | A | 1/1999 | Johnson et al. |
|---|---|---|---|
| 6,518,222 | B2 * | 2/2003 | Arndt et al. .................. 504/241 |
| 6,559,101 | B2 | 5/2003 | Johnson et al. |
| 2002/0013230 | A1 | 1/2002 | Emonds et al. |

FOREIGN PATENT DOCUMENTS

| WO | 2009457514 A1 | 4/2009 |
|---|---|---|
| WO | PCT/US2011/037633 | 5/2011 |

OTHER PUBLICATIONS

Chesterfield, Pyrimidines. Part XI. Synynthesis of 5-hydroxypyrimidine and related Compounds, 1960, Journal of the Chemical Society, p. 4590-4594.*
Chemical Hazard Properties Table of Hydrazine, obtained from http://cameochemicals.noaa.gov/chris/HDZ.pdf, accessed Feb. 16, 2012.*
Montgomery, 1-Deaza-6-methylthiopurine Ribonucleoside, 1966, J. Med. Chem., vol. 9, p. 354-357.*

* cited by examiner

*Primary Examiner* — Golam M M Shameem
*Assistant Examiner* — Karen Cheng
(74) *Attorney, Agent, or Firm* — Robert Chang; Craig E. Mixan

(57) ABSTRACT

5-Substituted-8-alkoxy[1,2,4]triazolo[1,5-c]pyrimidin-2-amines are manufactured from 2-substituted-4-amino-5-methoxypyrimidines in a process that avoids hydrazine and cyanogen halide.

4 Claims, No Drawings

PROCESS FOR THE PREPARATION OF 5-SUBSTITUTED-8-ALKOXY[1,2,4]TRIAZOLO[1,5-C]PYRIMIDIN-2-AMINES

CROSS REFERENCE TO RELATED APPLICATIONS

This application claims the benefit of U.S. Utility patent application Ser. No. 13/114,087 filed May 24, 2011 which claims the benefit of U.S. Provisional Patent Application Ser. No. 61/347,968 filed May 25, 2010.

BACKGROUND OF THE INVENTION

The present invention concerns a process for the preparation of 5-substituted-8-alkoxy[1,2,4]triazolo[1,5-c]pyrimidin-2-amines.

U.S. Pat. No. 6,005,108 describes certain substituted 5,8-disubstituted-[1,2,4]triazolo[1,5-c]pyrimidin-2-amine compounds and their use as intermediates for the preparation of sulfonamide herbicides. 5,8-Dimethoxy[1,2,4]triazolo[1,5-c]pyrimidin-2-amine is a useful intermediate for the preparation of penoxsulam. *Monatsh. Chem.* 1983, 114, 789 describes the preparation of certain (amino)carbonothioyl-carbamates followed by their reaction with hydroxylamine and subsequent cyclization to [1,2,4]triazolo[1,5-a]pyrimidin-2-amines. WO 2009/047514 A1 describes the preparation of certain (amino)carbonothioylcarbamates followed by their reaction with hydroxylamine and subsequent cyclization to [1,2,4]triazolo[1,5-a]pyridine and [1,2,4]triazolo[1,5-c]pyrimidine compounds. U.S. Pat. No. 6,559,101 B2 describes the preparation of certain (amino)carbonothioylcarbamates followed by their reaction with hydroxylamine and subsequent cyclization to pyrimidine substituted [1,2,4]triazolo[1,5-a]pyrimidin-2-amines.

5,8-Dimethoxy[1,2,4]triazolo[1,5-c]pyrimidin-2-amine is produced from 2,4-dichloro-5-methoxypyrimidine in a multistep process that involves both hydrazine and a cyanogen halide. Hydrazine presents a severe explosion hazard and is toxic by ingestion, inhalation and skin adsorption. It is classified as a carcinogen and has a TLV of 0.1 ppm in air. Cyanogen halides are highly irritating and very poisonous. It would be advantageous to produce 5-substituted-8-alkoxy[1,2,4]triazolo[1,5-c]pyrimidin-2-amines efficiently and in high yield by a manufacturing process that avoids hydrazine and cyanogen halide.

SUMMARY OF THE INVENTION

The present invention concerns the preparation of 5-substituted-8-alkoxy[1,2,4]triazolo[1,5-c]pyrimidin-2-amines from 2-substituted-4-amino-5-methoxypyrimidines. More particularly, the present invention concerns a process for the preparation of 5-substituted-8-alkoxy[1,2,4]triazolo[1,5-c]pyrimidin-2-amines of the formula (I),

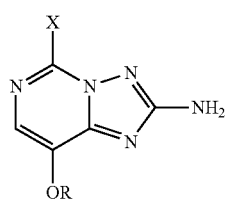

in which
X represents halogen or OR; and
R represents $C_1$-$C_4$ alkyl;
which comprises:
i) contacting a 2-substituted-4-amino-5-alkoxypyrimidine of the formula

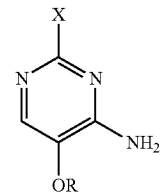

in which X and R are as previously defined
with an isothiocyanatidocarbonate of the formula

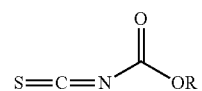

in which R is as previously defined,
in a polar aprotic solvent to provide a (pyrimidinylamino)carbonothioylcarbamate of the formula

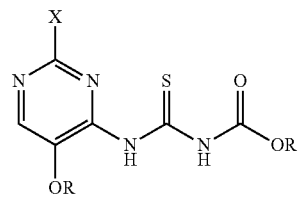

in which X and R are as previously defined;
ii) contacting the (pyrimidinylamino)carbonothioylcarbamate with hydroxylamine in the presence of a base to provide a (pyrimidinylamino)hydroxyimino)methylcarbamate of the formula

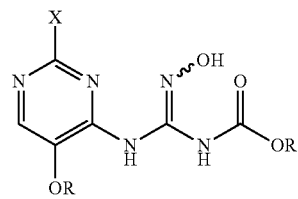

in which X and R are as previously defined; and
iii) cyclizing the (pyrimidinylamino)hydroxyimino)methylcarbamate by heating in an inert solvent to provide the 5-substituted-8-alkoxy-[1,2,4]triazolo[1,5-c]pyrimidin-2-amine.

In another embodiment of the invention, 5-halo-8-alkoxy[1,2,4]triazolo[1,5c]pyrimidin-2-amines can be converted into the corresponding 5,8-dialkoxy[1,2,4]triazolo[1,5-c]pyrimidin-2-amines by displacement of the halogen by an alkali metal alkoxide in an alcoholic solvent.

Another embodiment of the invention comprises a (pyrimidinylamino)carbonothioylcarbamate of the formula

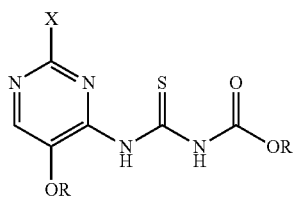

in which
X represents halogen or OR; and
R represents $C_1$-$C_4$ alkyl.

A further embodiment of the invention comprises a (pyrimidinylamino)hydroxyimino)methylcarbamate of the formula

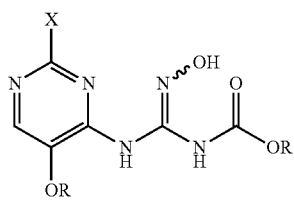

in which
X represents halogen or OR; and
R represents $C_1$-$C_4$ alkyl.

The material may exist as a pair of geometric isomers (E and Z), as well as in various tautomeric forms.

A further embodiment of the invention comprises a 5-halo-8-alkoxy[1,2,4]triazolo[1,5-c]pyrimidin-2-amines of the formula

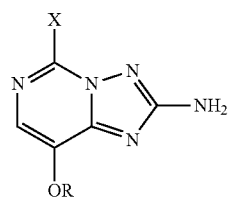

in which
X represents halogen; and
R represents $C_1$-$C_4$ alkyl.

DETAILED DESCRIPTION OF THE INVENTION

The term alkyl and derivative terms such as alkoxy, as used herein refer to straight chain or branched chain groups. Typical alkyl groups are methyl, ethyl, propyl, 1-methylethyl, butyl, 1,1-dimethylethyl and 1-methylpropyl. Methyl and ethyl are often preferred. The term halogen, as used herein, refers to fluorine, chlorine, bromine and iodine. A chloro group is often preferred.

The 2-substituted-4-amino-5-alkoxypyrimidine and the alkyl isothiocyanatidocarbonate starting materials are known compounds or can be prepared by procedures well known to those of ordinary skill in the art.

The present invention concerns the preparation of 5-substituted-8-alkoxy[1,2,4]triazolo[1,5-c]pyrimidin-2-amines from 2-substituted-4-amino-5-methoxypyrimidines.

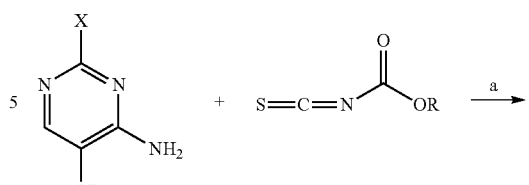

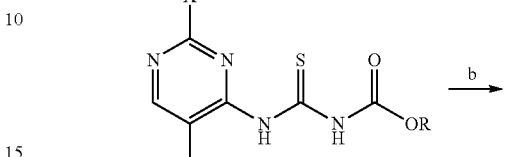

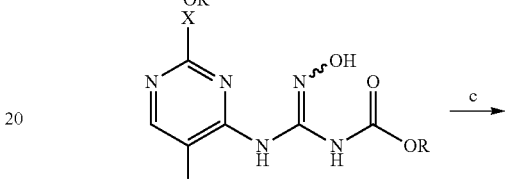

The first step of the present invention (a) concerns the conversion of a 4-aminopyrimidine in which
X represents halogen or OR and
R represents $C_1$-$C_4$ alkyl
to a (pyrimidinylamino)carbonothioylcarbamate. This is accomplished using at least one equivalent and preferably an excess of isothiocyanatidocarbonate in a polar aprotic solvent, preferably acetonitrile or ethyl acetate. It is also possible to perform the reaction in the presence of additional diluents, provided those diluents do not interfere with the desired reaction and are chemically inert to the reactants. The isothiocyanatidocarbonate is added at a temperature from 0° C. to room temperature; the mixture is generally heated to some temperature between room temperature and reflux of the diluent added, preferably to reflux. The product is isolated by conventional techniques, such as by filtration of a precipitated or crystallized material.

In a typical reaction, the aminopyrimidine is dissolved or suspended in ethyl acetate and then treated with the appropriate amount of the isothiocyanatidocarbonate. After heating to reflux, the reaction mixture is cooled to a temperature at which the desired compound precipitates and is collected by filtration and dried. Optionally, some or most of the solvent may be removed by distillation prior to filtration to improve crystal filtration or reduce solubility of the product in the solvent and thereby improve recovery.

The second step of the present invention (b) concerns the conversion of the (pyrimidinylamino)carbonothioylcarbamate to its (pyrimidinylamino)hydroxyimino)methylcarbamate equivalent. This is accomplished using at least an equivalent of hydroxylamine, preferably as a salt, and a base, such as sodium or potassium carbonate, sodium or potassium hydroxide or a trialkylamine. Sodium carbonate or sodium hydroxide are the preferred auxiliary bases. It is not uncommon to use up to 4 equivalents of hydroxylamine and base in this reaction. The reaction mixture is diluted with water and a polar solvent, preferably ethyl acetate or acetonitrile and is stirred at a temperature between 0° C. and 35° C., preferably at room temperature. It is also possible to perform the reaction in the presence of additional diluents, provided those diluents do not interfere with the desired reaction and are chemically inert to the reactants. The product is optionally cooled and is isolated by conventional techniques, such as collection by filtration and drying or flash-chromatography. The material may exist as an E/Z isomeric mixture and/or in various tautomeric forms. Optionally, rather than isolating the (pyrimidinylamino)hydroxyimino)methylcarbamate, the reaction may be retained as the reaction mixture and heated to effect the cyclization to the 5-substituted-8-alkoxy[1,2,4]triazolo [1,5-c]pyrimidin-2-amines and isolated according to the details below.

In a typical reaction, the (pyrimidinylamino)carbonothioylcarbamate, hydroxylamine and base are dissolved in water and either acetonitrile or ethyl acetate. The reaction mixture is stirred at room temperature and then is either heated to convert to the 5-substituted-8-alkoxy[1,2,4]triazolo [1,5-c]pyrimidin-2-amine, or filtered and recrystallized from acetonitrile, to isolate the (pyrimidinylamino)hydroxyimino) methylcarbamate. Optionally, some or most of the solvent may be removed by distillation prior to filtration to improve crystal filtration or reduce solubility of the product in the solvent and thereby improve recovery.

The third step of this invention (c) concerns the conversion of the optionally isolated (pyrimidinylamino)hydroxyimino) methylcarbamate to the 5-substituted-8-alkoxy[1,2,4]triazolo[1,5-c]pyrimidin-2-amine using heat and an inert solvent. It is often preferable to convert the (pyrimidinylamino) hydroxyimino)methylcarbamate to the 5-substituted-8-alkoxy[1,2,4]triazolo[1,5-c]pyrimidin-2-amine without isolation. This conversion is accomplished by heating the reaction mixture. The product is optionally cooled and is isolated by conventional techniques, such as collection by filtration and drying.

Another embodiment of the invention concerns the conversion (d) of the 5-halo-8-alkoxy[1,2,4]triazolo[1,5-c]pyrimidin-2-amine

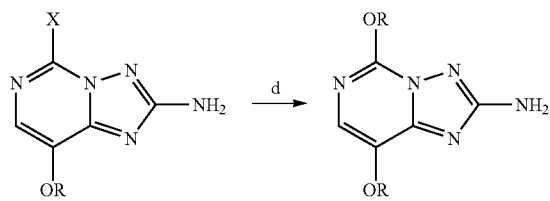

in which
X represents halogen; and
R represents $C_1$-$C_4$ alkyl
to its alkoxy analog, 5,8-alkoxy[1,2,4]triazolo[1,5-c]pyrimidin-2-amine, using at least one equivalent and preferably an excess of sodium or potassium methoxide in an alcohol solvent. It is also possible to perform the reaction in the presence of additional diluents, provided those diluents do not interfere with the desired reaction and are chemically inert to the reactants. The mixture is stirred at some temperature between 0° C. and 50° C., with room temperature being preferred. The product is optionally cooled and is isolated by conventional techniques, such as collection by filtration and drying.

In a typical reaction, the 5-chloro-8-alkoxy[1,2,4]triazolo [1,5-c]pyrimidin-2-amine is taken up in acetonitrile at room temperature and treated with 25% sodium methoxide in methanol. The resulting slurry is stirred at room temperature for several hours and then filtered and dried to afford 5-methoxy-8-alkoxy[1,2,4]triazolo[1,5-c]pyrimidin-2-amine. Optionally, some or most of the solvent may be removed by distillation prior to filtration to improve crystal filtration or reduce solubility of the product in the solvent and thereby improve recovery.

The following examples are presented to illustrate the invention.

EXAMPLES

All reagents described were obtained commercially and used without additional purification. HPLC analyses were done on a Perkin Elmer Series 200 instrument with Diode-array ultraviolet detector. A Zorbax RX-C8 column was used, employing various ratios of acetonitrile-water modified with 0.1% phosphoric acid as eluant at a flow rate of 1 mL/min and ultraviolet detection at 220 nm Nuclear magnetic resonance spectra were obtained on a Bruker AC 300 NMR spectrometer (300 MHz). Mass spectral data was obtained using accurate mass electrospray liquid chromatography—mass spectrometry (ESI/LC/MS) in the positive ion (PI) mode and accurate mass electrospray liquid chromatography—mass spectrometry—mass spectrometry (ESI/LC/MS/MS).

Example 1

Preparation of Ethyl [2-chloro-5-methoxypyrimidin-4-yl)amino]-carbonothioylcarbamate (2)

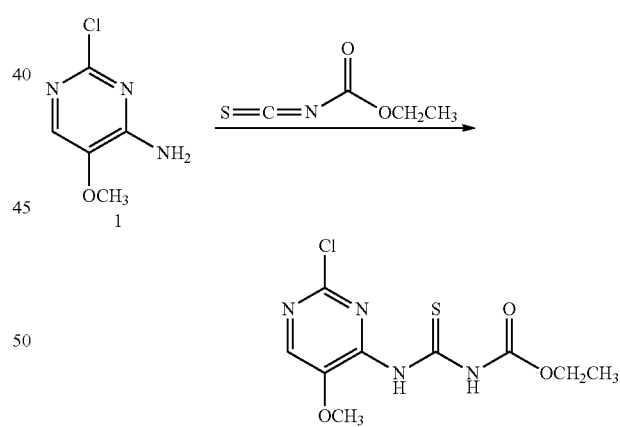

2-Chloro-5-methoxypyrimidin-4-amine (1) (6.4 g, 0.040 mol) was suspended in ethyl acetate (100 mL) and heated to near reflux. Ethyl isothiocyanatidocarbonate (8.9 g, 1.7 eq) was added all at once, and the mixture was maintained at reflux for 10 hours. The resulting slurry was cooled to 15° C., and the solid product was isolated by filtration and the cake washed with fresh ethyl acetate to afford the title compound in several crops as a solid (7.8 g, 67%): mp 182° C.; $^1$H NMR (DMSO-$d_6$): δ 11.97 (s, 1H), 11.72 (s, 1H), 8.50 (s, 1H), 4.22 (q, 2H), 3.72 (s, 3H), 1.17 (t, 3H); $^{13}$C NMR (DMSO-$d_6$): δ 177.82, 153.58, 150.00, 149.01, 144.26, 142.63, 62.76, 57.56, 14.44; Mass spec (accurate mass): Calcd for $C_9H_{11}ClN_4O_3S$: 290.024039; found, 290.0241.

Example 2

Preparation of Ethyl (Z and E)-[(2-chloro-5-methoxypyrimidin-4-yl)-amino](hydroxyimino)methylcarbamate (3)

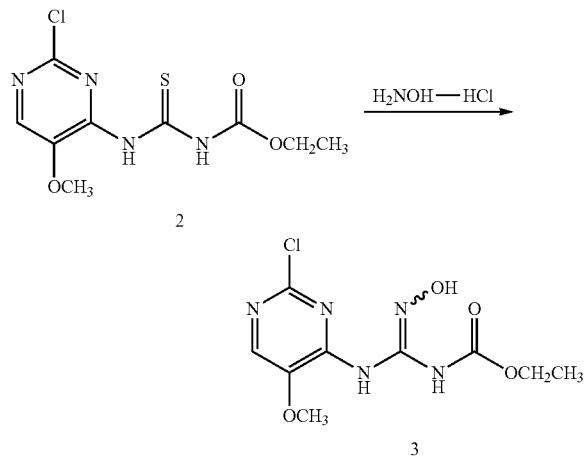

Hydroxylamine hydrochloride (280 mg, 4 eq) and sodium bicarbonate (335 mg, 4 eq) were combined and dissolved in water (6 mL) at room temperature. To this was added a suspension of ethyl [(2-chloro-5-methoxypyrimidin-4-yl)amino]carbonothioylcarbamate (2; 290 mg, 1.0 mmol) in acetonitrile (15 mL). The resulting slurry was stirred at room temperature for 1 hour, and the solids were then collected by filtration. Recrystallization from acetonitrile afforded the title compound as a light yellow solid (170 mg, 59%): mp 183-184° C. (dec); $^1$H NMR (DMSO-$d_6$) (mixture of isomers) δ 10.77 (s, 0.6H), 10.5 (s, 0.4H), 9.48 (s, 0.6H), 9.34 (s, 0.4H), 9.09 (s, 0.4H), 8.40 (s, 0.6H), 8.11 (s, 0.6H), 8.11 (s, 0.6H), 7.95 (s, 0.4H) 4.19-3.89 (m, 5H), 1.17-1.09 (m, 3H); $^{13}$C NMR (DMSO-$d_6$): δ 154.4, 154.0, 149.9, 140.2, 140.0, 139.1, 138.6, 138.0, 61.2, 60.9, 57.3, 56.5, 14.8, 14.5; Mass spec (accurate mass): Calcd for $C_9H_{12}ClN_5O_4$ 289.05778; found, 289.0577.

Example 3

Preparation of 5-Chloro-8-methoxy[1,2,4]triazolo[1,5-c]pyrimidin-2-amine (4) without Isolation of (3)

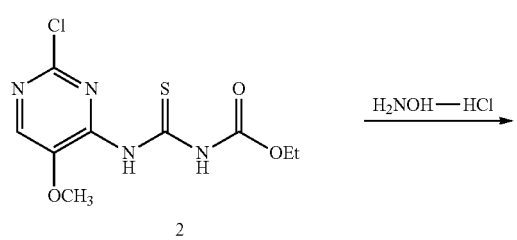

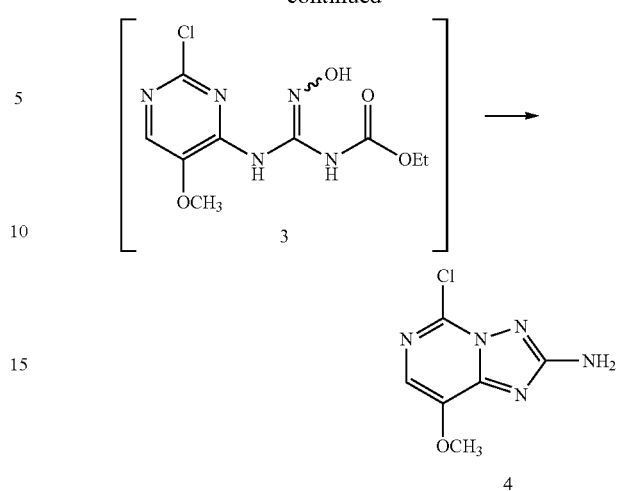

Ethyl [(2-chloro-5-methoxypyrimidin-4-yl)amino]carbonothioylcarbamate (2) (290 mg, 1.0 mmol), hydroxylamine hydrochloride (143 mg, 2 eq), and sodium bicarbonate (170 mg, 2 eq) were combined. Water (5 mL) and acetonitrile (5 mL) were added at room temperature. The resulting slurry was stirred at room temperature overnight, then treated with 20 drops of saturated aqueous sodium carbonate solution. The resulting solution was sparged with nitrogen and cooled, producing the product as a chalky precipitate, which was collected by filtration (in two crops), washed with water, and dried to obtain the title compound as a solid (139 mg, 68%): mp 251° C.; $^1$H NMR (DMSO-$d_6$) δ 7.73 (s, 1H), 3.98 (s 3H); 6.63 (s, 2H); $^{13}$C NMR (DMSO-$d_6$): 166.30, 148.14, 128.91, 124.67, 57.51; Mass spec (accurate mass): Calcd for $C_6H_6ClN_5O$ 199.026087; found, 199.0256.

Example 4

Preparation of 5-chloro-8-methoxy[1,2,4]triazolo[1,5-c]pyrimidin-2-amine (4) Without Isolation of (3)

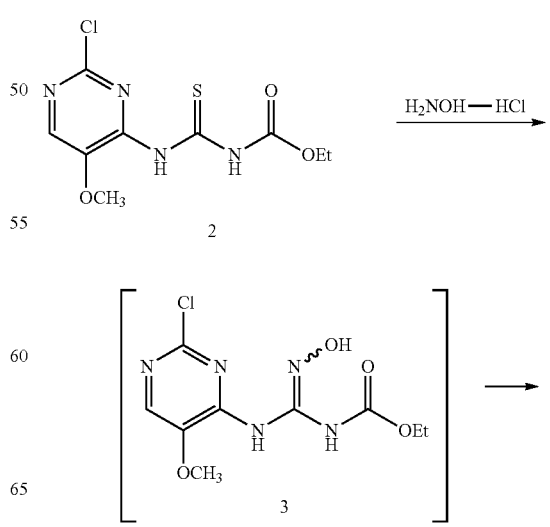

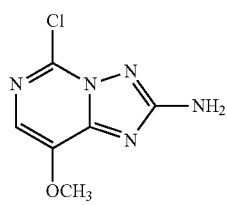

Hydroxylamine hydrochloride (280 mg, 4 eq), and sodium bicarbonate (210 mg, 2.5 eq) were combined in water (5 mL) and stirred for 5 minutes. Ethyl [(2-chloro-5-methoxypyrimidin-4-yl)amino]carbonothioylcarbamate (2) (290 mg, 1.0 mmol), suspended in t-butanol (15 mL) was added at room temperature. The reaction was stirred at room temperature for 5 hours, and then treated with 10 drops of saturated aqueous sodium carbonate solution. The reaction slurry was then filtered, and the product solids washed with water and dried to obtain the title compound as a off white solid (330 mg, 83%) that was identical in HPLC retention to previously described 5-chloro-8-methoxy[1,2,4]triazolo-[1,5-c]pyrimidin-2-amine (4).

Example 5

Preparation of 5,8-dimethoxy[1,2,4]triazolo[1,5-c]pyrimidin-2-amine (5)

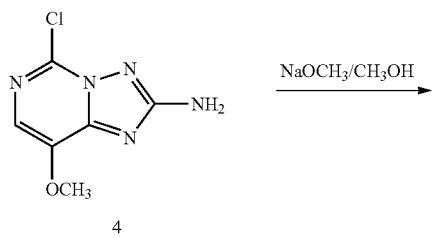

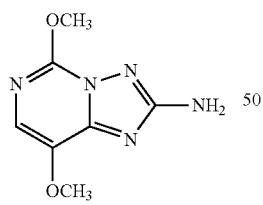

5-Chloro-8-methoxy[1,2,4]triazolo[1,5-c]pyrimidin-2-amine (4; 100 mg, 0.50 mmol) was suspended in acetonitrile (5 mL) at room temperature and treated with 25% sodium methoxide in methanol (200 mg, 2 eq). The resulting slurry was stirred at room temperature for 1.5 hours and then filtered. The solids were washed with water and dried to afford the title compound as a chalk-colored solid (87 mg, 88%) that was identical in HPLC retention to authentic 5,8-dimethoxy[1,2,4]triazolo[1,5-c]pyrimidin-2-amine (5): mp 185-186° C.; $^1$H NMR (DMSO-d$_6$) δ 7.48 (s, 1H), 6.38 (br s, 2H), 4.04 (s, 3H), 3.88 (s, 3H); EIMS m/z 195.

Example 6

Preparation of Ethyl [(2,5-dimethoxypyrimidin-4-yl)amino]carbonothioylcarbamate

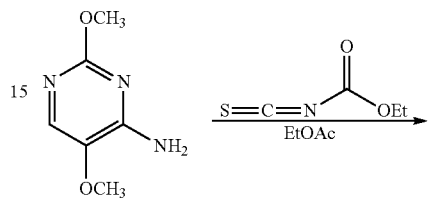

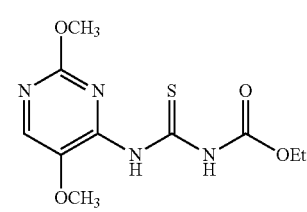

2,5-Dimethoxypyrimidin-4-amine (6) (3 g, 0.0193 moles) was dissolved in 18 g of ethyl acetate. Ethyl isothiocyanatidocarbonate (2.77 g, 0.0208 moles) was added in one portion. The solution was heated to 78° C. and held at that temperature for 11 h. An additional 1.4 g of the ethyl isothiocyanatidocarbonate was added and the mixture heated for 2.5 h. The mixture was allowed to cool to 22° C. and filtered. The resulting solid was washed with ethyl acetate (20 mL) and dried to a constant weight in a fume hood to afford the title compound as a yellow solid (4.81 g, 89%): $^{13}$C NMR (DMSO-d$_6$, 100 MHz) δ 177.5, 158.4, 153.3, 149.5, 142.3, 139.5, 62.6, 57.6, 55.2, 14.4; HRMS (ESI), calcd for C$_{10}$H$_{14}$N$_4$O$_4$S, 286.0736; found, 286.0727.

Example 7

Hydroxylamine Addition to Produce 8 and Cyclization to Form 5,8-dimethoxy[1,2,4]triazolo[1,5-c]pyrimidin-2-amine (5)

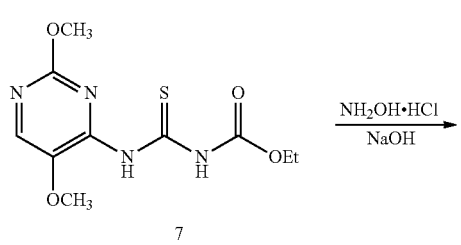

-continued

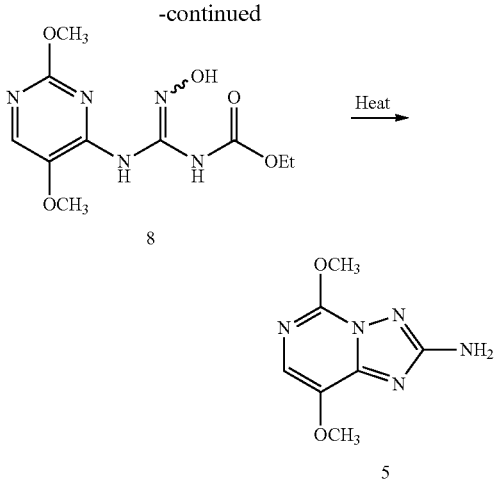

8

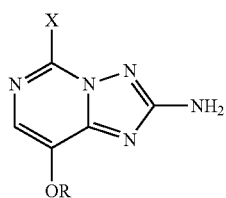

5

Ethyl [(2,5-dimethoxypyrimidin-4-yl)amino]carbonothioylcarbamate (7; 4.30 g, 0.0154 moles) was dispersed in 24 g of ethyl acetate. Hydroxylamine hydrochloride (1.28 g, 0.0193 moles), water (3.84 g), and 2M NaOH (12.61 g, 0.0252 moles) were then added to the stirring slurry. The internal temperature rose to 26° C. after the NaOH was added. Ethyl (E/Z)-[(2-chloro-5-methoxy-pyrimidin-4-yl)amino](hydroxyimino)methylcarbamate (8) was not isolated but was heated to 50° C. to cyclize. The mixture was cooled to room temperature and allowed to stir overnight. The slurry was filtered at room temperature and the cake was washed with water (3×8 g) and dried to a constant weight in the fume hood providing the title compound as a tan solid (3.16 g, 105% yield by weight). The major component had a retention time identical to authentic 5,8-dimethoxy[1,2,4]-triazolo[1,5-c]pyrimidin-2-amine (5). In a separate experiment ethyl (E/Z)-[(2,5-dimethoxypyrimidin-4-yl)amino](hydroxyimino)methylcarbamate (8) was isolated via chromatography on silica gel (chloroform as the eluent) providing a white solid (0.4 g, 13%), which was a ca. 77/23 mixture of geometric isomers: $^1$H NMR (DMSO-$d_6$) (mixture of isomers) δ 10.65 (s, 1H), 10.34 (s, 0.3H), 9.56 (s, 1H), 8.98 (s, 0.3H), 8.94 (s, 0.3H), 8.20 (s, 1H), 8.00 (s, 1H), 7.82 (s, 0.3H), 4.25-3.90 (m, 2.6 H), 3.88 (s, 3H), 3.81 (s, 0.9H), 3.78 (s, 3H), 3.22 (s, 0.9H), 1.20-1.15 (m, 3H); Mass spec (accurate mass): Calcd for $C_9H_{12}ClN_5O_4$ 289.0578; found, 289.0571.

What is claimed is:

1. A process for the preparation of 5-substituted-8-alkoxy[1,2,4]triazolo[1,5-c]-pyrimidin-2-amines of the formula (I),

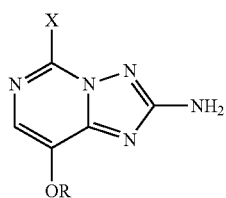

(I)

in which
X represents halogen or OR; and
R represents $C_1$-$C_4$ alkyl;

which comprises:
i) contacting a 2-substituted-4-amino-5-alkoxypyrimidine of the formula

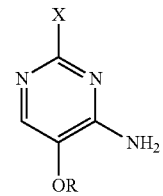

in which X and R are as previously defined
with an isothiocyanatidocarbonate of the formula

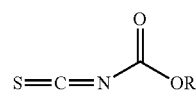

in which R is as previously defined,
in a polar aprotic solvent to provide a (pyrimidinylamino)carbonothioylcarbamate of the formula

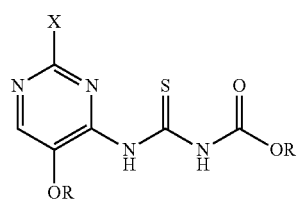

in which X and R are as previously defined;
ii) contacting the (pyrimidinylamino)carbonothioylcarbamate with hydroxylamine in the presence of a base to provide a (pyrimidinylamino)hydroxyimino)methylcarbamate of the formula

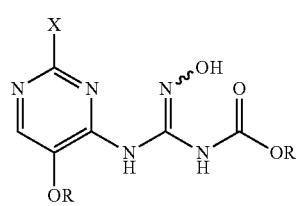

in which X and R are as previously defined; and
iii) cyclizing the (pyrimidinylamino)hydroxyimino)methylcarbamate by heating in an inert solvent to provide the 5-substituted-8-alkoxy[1,2,4]triazolo[1,5-c]pyrimidin-2-amine.

2. The process of claim 1 in which X and R both represent $OCH_3$.

3. The process of claim 1 in which the (pyrimidinylamino)(hydroxyimino)-methylcarbamate of step ii) is used without isolation to prepare the 2-amino-5-substituted-8-alkoxy[1,2,4]triazolo[1,5-c]pyrimidine in step iii).

4. A process for the preparation of 2-amino-5,8-alkoxy[1,2,4]triazolo[1,5-c]pyrimidines of the formula

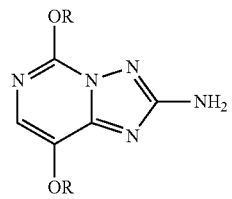

in which
R represents $C_1$-$C_4$ alkyl;
which comprises contacting a 5-halo-8-alkoxy[1,2,4]triazolo[1,5-c]pyrimidin-2-amine of the formula

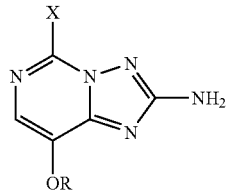

in which
X represents halogen; and
R represents $C_1$-$C_4$ alkyl
with an alkali metal alkoxide in an alcoholic solvent.

* * * * *